US008202215B2

(12) United States Patent
Xiao et al.

(10) Patent No.: US 8,202,215 B2
(45) Date of Patent: Jun. 19, 2012

(54) PHARYNGEAL INTUBATION GUIDING DEVICE

(75) Inventors: Bo-Wen Xiao, Taichung (TW);
Tzu-Chieh Lin, Taichung (TW);
Feng-Min Lai, Taichung (TW);
Chung-Chih Lin, Taichung (TW)

(73) Assignees: Plastics Industry Development Center, Taichung County (TW); Pontex Polyblend Co., Ltd., Taichung (TW)

( * ) Notice: Subject to any disclaimer, the term of this patent is extended or adjusted under 35 U.S.C. 154(b) by 220 days.

(21) Appl. No.: 12/704,175

(22) Filed: Feb. 11, 2010

(65) Prior Publication Data

US 2011/0196203 A1    Aug. 11, 2011

(51) Int. Cl.
*A61B 1/267* (2006.01)
(52) U.S. Cl. ......... 600/194; 600/120; 600/185; 600/190
(58) Field of Classification Search .................. 600/120, 600/185–200, 104, 107; 128/200.26, 200.29
See application file for complete search history.

(56) References Cited

U.S. PATENT DOCUMENTS

| 4,982,729 | A  | * | 1/1991  | Wu ............................... 600/187 |
| 5,261,392 | A  | * | 11/1993 | Wu ............................... 600/188 |
| 7,988,622 | B2 | * | 8/2011  | Achas Gandarias ........... 600/188 |
| 2006/0276694 | A1 | * | 12/2006 | Acha Gandarias ........... 600/194 |
| 2007/0106122 | A1 | * | 5/2007  | Yokota et al. .................. 600/188 |
| 2007/0129607 | A1 | * | 6/2007  | Ashfaque ....................... 600/194 |
| 2008/0156324 | A1 | * | 7/2008  | Isenberg et al. ........... 128/200.26 |
| 2009/0143645 | A1 | * | 6/2009  | Matthes ........................ 600/120 |
| 2010/0249639 | A1 | * | 9/2010  | Bhatt ............................ 600/546 |
| 2010/0288272 | A1 | * | 11/2010 | Yokota et al. ............. 128/200.26 |
| 2011/0077466 | A1 | * | 3/2011  | Rosenthal ..................... 600/188 |

FOREIGN PATENT DOCUMENTS

| EP | 1982640     | 10/2008 |
| WO | 2007/085664 | 8/2007  |

* cited by examiner

*Primary Examiner* — Eduardo C Robert
*Assistant Examiner* — Jan Christopher Merene
(74) *Attorney, Agent, or Firm* — Renner, Otto, Boisselle & Sklar, LLP

(57) ABSTRACT

A pharyngeal intubation guiding device includes lengthwise extending tongue-side and palate-side walls that cooperatively define a guiding duct. The tongue-side wall is configured to conform to the rear end of a patient's tongue to permit the guiding duct to confront the opening of the patient's larynx. The palate-side wall has an outer contour which establishes a guideway towards the opening of the patient's esophagus. A lengthwise extending laryngoscope guiding channel and a lengthwise extending endotracheal tube guiding groove are disposed in the guiding duct. A viewing window is disposed to define a terminal end of the laryngoscope guiding channel. The endotracheal tube guiding groove has a lead-in port to permit an endotracheal tube introduced therein to be removable laterally. A lengthwise extending conduit is disposed in the guiding duct to permit an aspirator tube to reach the patient's trachea to suck out phlegm.

9 Claims, 9 Drawing Sheets

PHARYNGEAL INTUBATION GUIDING DEVICE

BACKGROUND OF THE INVENTION

1. Field of the Invention

This invention relates to a medical device, more particularly to a pharyngeal intubation guiding device for guiding insertion of an endotracheal tube into a trachea of a patient.

2. Description of the Related Art

Referring to FIG. 1, a conventional disposable laryngeal mask airway device 1 is shown to include an airway tube and a cuff connected to one end of the airway tube for facilitating placement of the airway tube into the trachea of a patient. However, this technique requires significant operator skill and experience. Unskilled and emergency insertion may cause injuries to the patient.

Referring to FIG. 2, another conventional laryngeal medical device 2 disclosed in WO 2007/085664 is shown to include a longitudinal body which is internally divided into two independent conduits 201,202 separately by a central partition. The endotracheal conduit 201 is used for inserting an endotracheal tube, and the viewing conduit 202 is used for viewing the trachea where the endotracheal tube is to be inserted. The endotracheal conduit 201 has upper and lower walls 203,205, and a plurality of side walls 204 extending parallel to the central partition to allow the endotracheal tube to slide through the endotracheal conduit 201 without coming out of such conduit 201 and to allow the subsequent removal of the tube. However, the side walls 204 project from the edges of the upper and lower walls 203,205, and may injure the patient during intubation.

SUMMARY OF THE INVENTION

An object of the present invention is to provide a pharyngeal intubation guiding device which facilitates pharyngeal intubation and which is convenient to assemble and safe to use.

According to this invention, the pharyngeal intubation guiding device includes tongue-side and palate-side walls which extend in a lengthwise direction, and which are spaced apart from each other in a direction transverse to the lengthwise direction to define a guiding duct. The tongue-side wall has first entry and locating ends opposite to each other in the lengthwise direction, and first prepharyngeal and postpharyngeal segments which extend respectively from the first entry end and first locating ends and towards each other to form a first juncture region. The first juncture region is configured to conform to the rear end of a patient's tongue such that the first locating end is brought to engage the front of the patient's epiglottis to thereby permit the guiding duct of the postpharyngeal segment to confront the opening of the patient's larynx. The palate-side wall has second entry and locating ends which are opposite to each other in the lengthwise direction, and second prepharyngeal and postpharyngeal segments which extend respectively from the second entry end and the second locating end and towards each other to form a second juncture region. The first and second entry ends cooperatively define an access opening which is in spatial communication with the guiding duct. The second locating end is configured to be disposed at the opening of the patient's larynx to serve as a barrier between the larynx and the esophagus of the patient when the first locating end is engaged with the front of the patient's epiglottis. The second juncture region is configured such that an outer contour of the second prepharyngeal segment establishes a guideway towards the opening of the patient's esophagus. A laryngoscope guiding channel is disposed in the guiding duct, and extends from the first postpharyngeal segment to the first prepharyngeal segment and through the access opening. A viewing window extends between the first and second postpharyngeal segments in the transverse direction so as to define a terminal end of the laryngoscope guiding channel that is located upstream of the first locating end. An endotracheal tube guiding groove is disposed in the guiding duct, and extends from the first locating end along the first postpharyngeal and prepharyngeal segments and to a lead-in port. The lead-in port is configured to be located laterally and outwardly of the access opening so as to permit an endotracheal tube introduced therein to be removable laterally between the first and second prepharyngeal segments.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
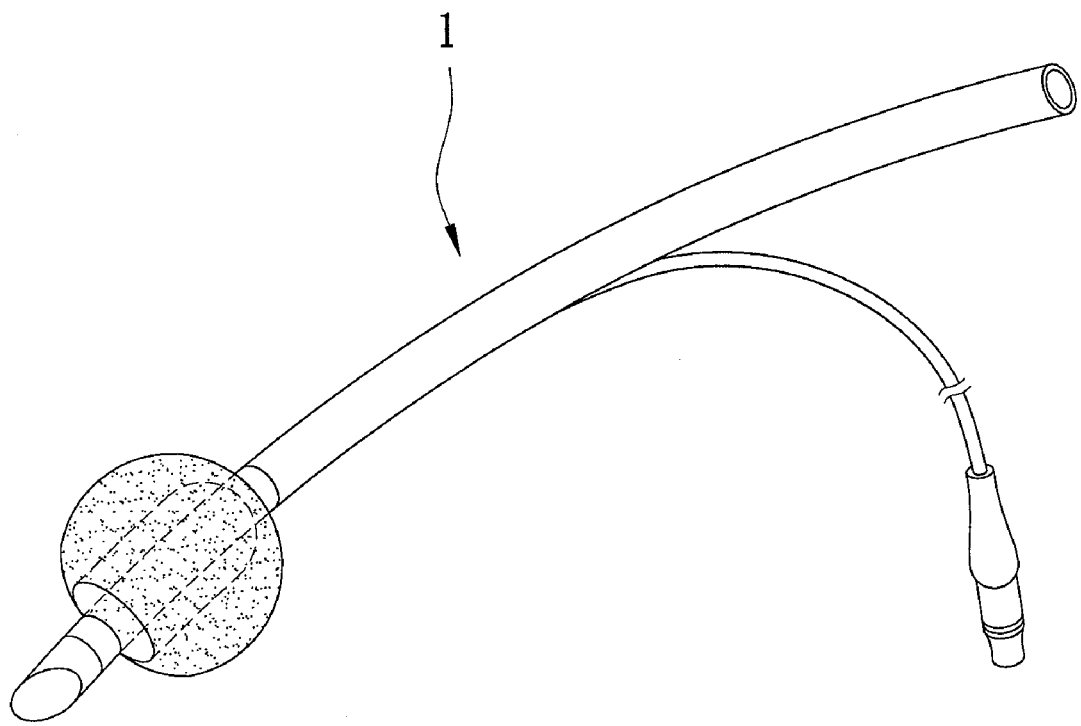
FIG. 1 is a perspective view of a conventional disposable laryngeal mask airway device.
Figure 2:
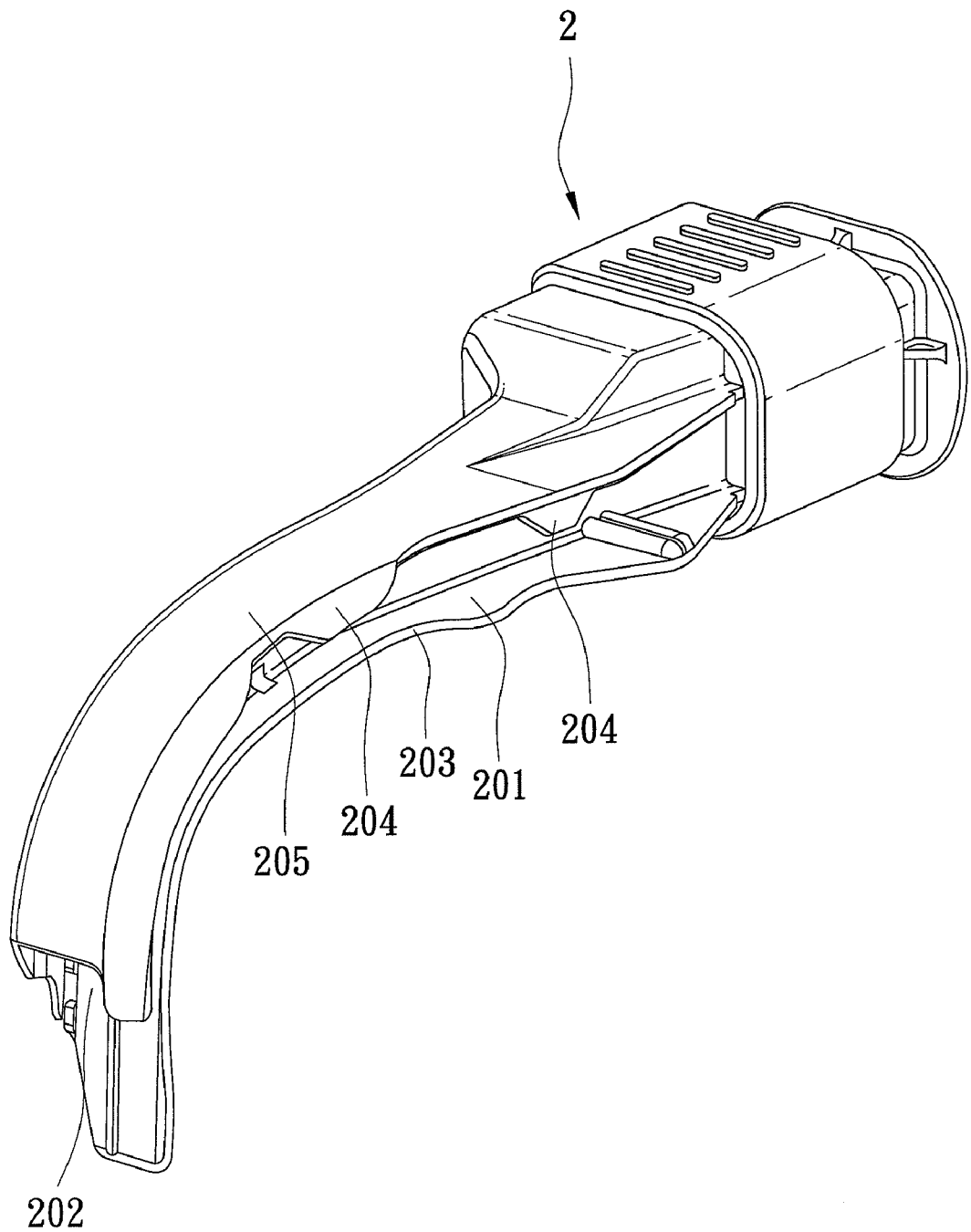
FIG. 2 is a perspective view of another conventional laryngeal medical device.
Figure 3:
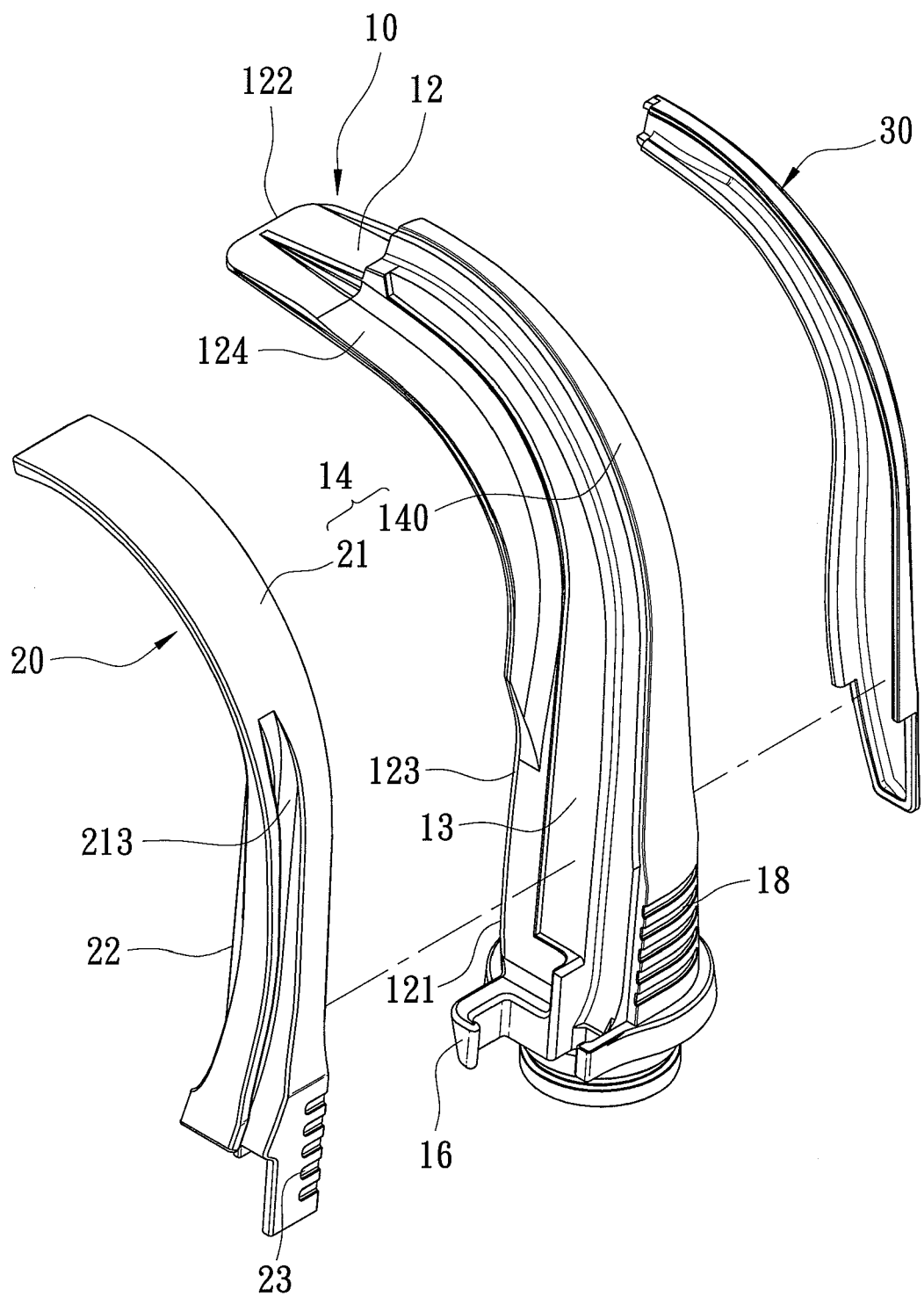
FIG. 3 is an exploded perspective view of the preferred embodiment of a pharyngeal intubation guiding device according to this invention.

Referring to FIGS. 3 to 6 and 9, the preferred embodiment of a pharyngeal intubation guiding device according to the present invention is shown to comprise a first shell 10, a second shell 20, and a cover wall 30, each of which is made of a transparent plastic material by an injection molding process to have a single-piece construction.

The pharyngeal intubation guiding device according to this embodiment includes tongue-side and palate-side walls 12,14 which extend in a lengthwise direction, and which are spaced apart from each other in a direction transverse to the lengthwise direction to define a guiding duct, a partition wall 13, a viewing window 15, and a juxtaposed wall 22.

The tongue-side wall 12 has first entry and locating ends 121,122 opposite to each other in the lengthwise direction, and first prepharyngeal and postpharyngeal segments 123, 124 extending respectively from the first entry end 121 and the first locating end 122 and towards each other to form a first juncture region 125 which is configured to conform to the rear end of a patient's tongue such that the first locating end 122 is brought to engage the front of the patient's epiglottis to thereby permit the guiding duct at the first postpharyngeal segment 124 to confront the opening of the patient's larynx.

The palate-side wall 14 has second entry and locating ends 141,142 which are opposite to each other in the lengthwise direction. The second entry end 141 cooperates with the first entry end 121 to define an access opening 111 which is in spatial communication with the guiding duct. The second locating end 142 is configured to be disposed at the opening of the patient's larynx to serve as a barrier between the larynx and the esophagus of the patient when the first locating end 122 is engaged with the front of the patient's epiglottis. The palate-side wall 14 further includes second prepharyngeal and postpharyngeal segments 143,144 extending respectively from the second entry end 141 and the second locating end 142 and towards each other to form a second juncture region 145. In this embodiment, the palate-side wall 14 includes channel-side and groove-side wall sections 140,21 which are attachable to each other along a joining line extending in the lengthwise direction.

Figure 4:
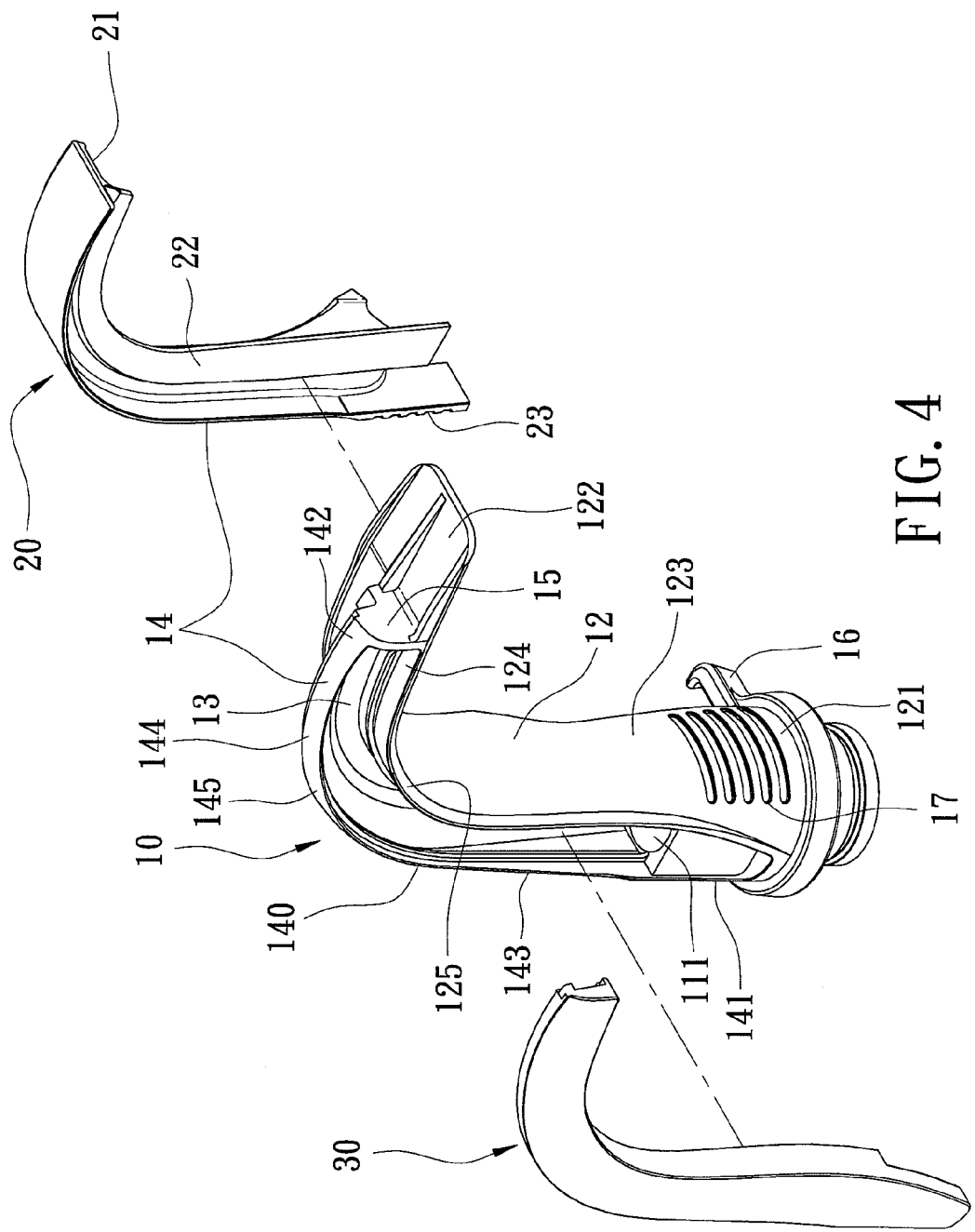
FIG. 4 is an exploded perspective view of the preferred embodiment taken from another angle.
Figure 5:
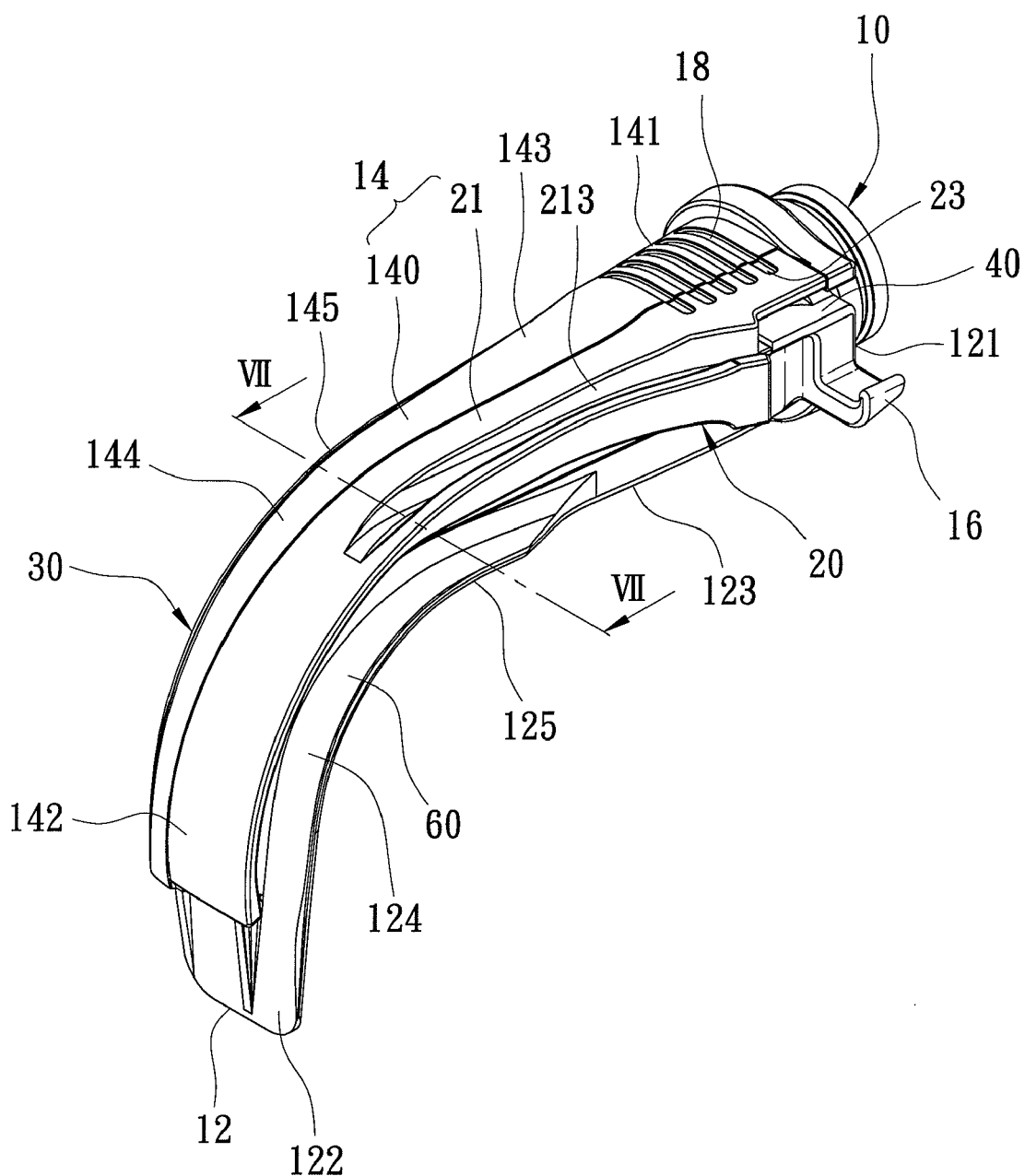
FIG. 5 is a perspective view of the preferred embodiment.
Figure 7:
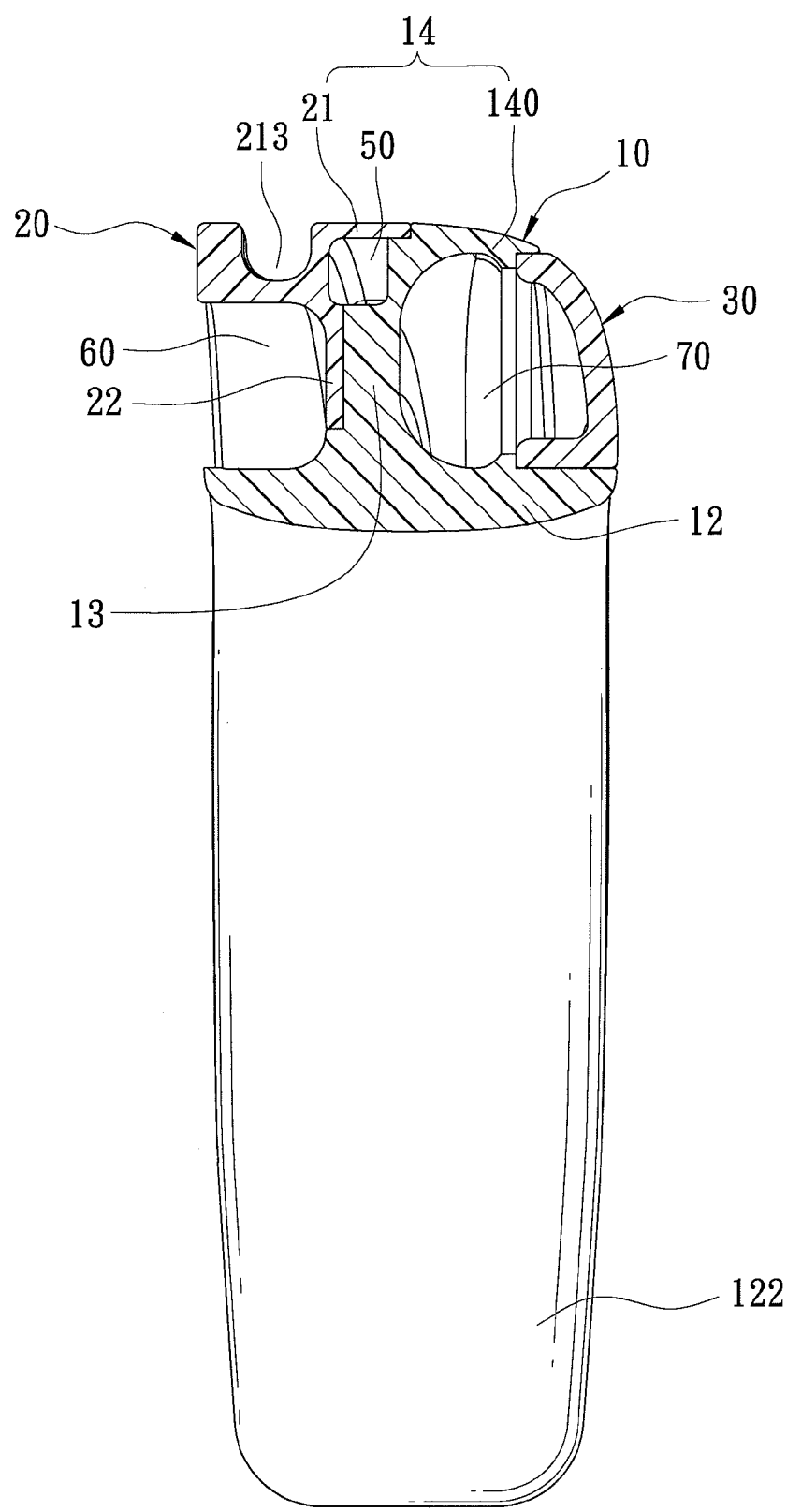
FIG. 7 is a sectional view taken along line VII-VII of FIG. 5.
Figure 8:
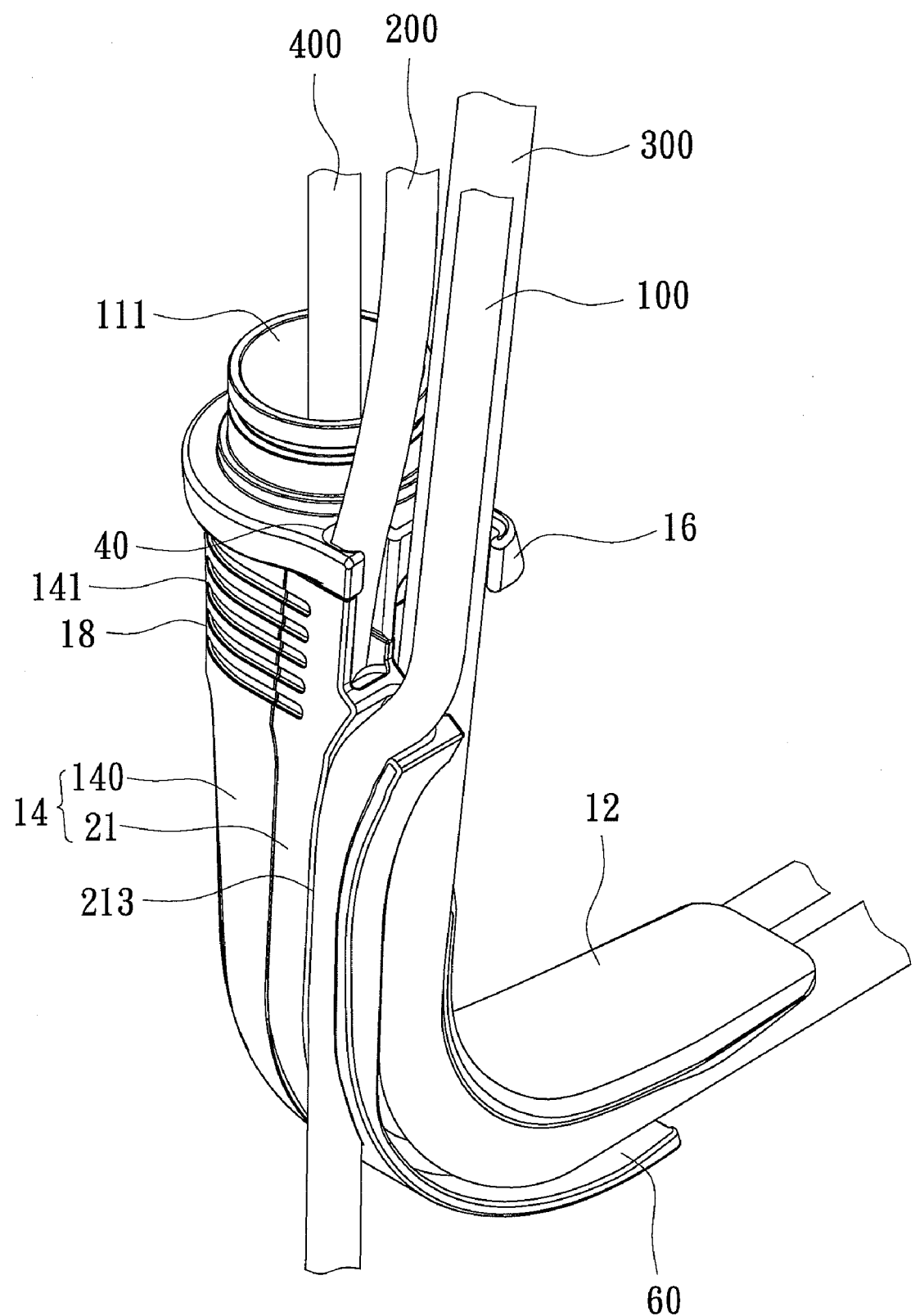
FIG. 8 is a perspective view of the preferred embodiment in a state of use.
Figure 9:
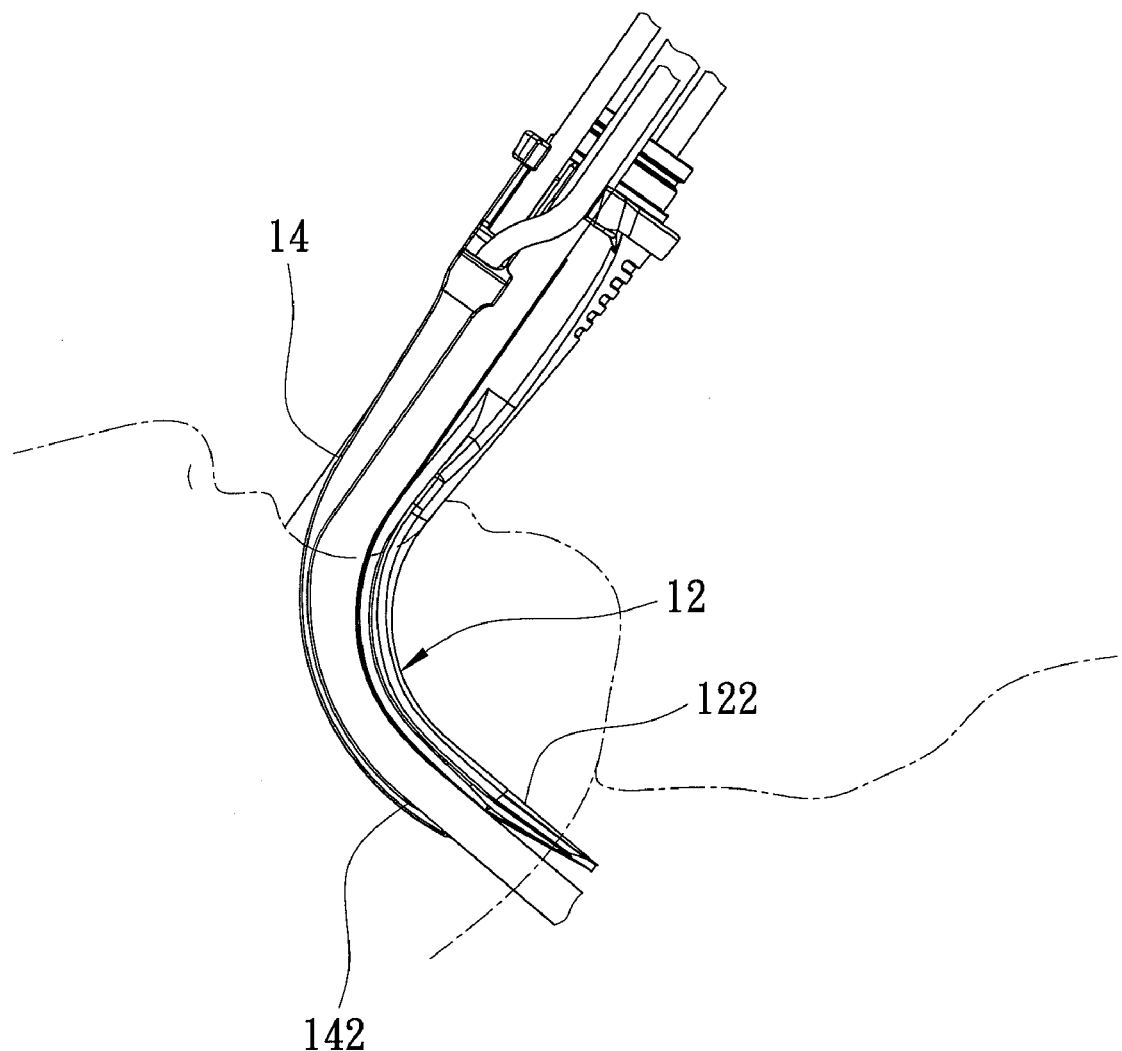
FIG. 9 is a schematic view of the preferred embodiment in the state of use.

With reference to FIGS. 4 and 7, the partition wall 13 extends between the tongue-side wall 12 and the palate-side wall 14 and in the lengthwise direction so as to divide the guiding duct into a laryngoscope guiding channel 70 and an endotracheal tube guiding groove 60 at the channel-side wall section 140 and the groove-side wall section 21, respectively. Specifically, the laryngoscope guiding channel 70 extends from the first postpharyngeal segment 124 to the first prepharyngeal segment 123 and through the access opening 111. The viewing window 15 is made of a transparent plastic material, and extends between the first and second postpharyngeal segments 124,144 in the transverse direction so as to define a terminal end of the laryngoscope guiding channel 70 that is located upstream of the first locating end 122. The endotracheal tube guiding groove 60 extends from the first locating end 122 along the first postpharyngeal and prepharyngeal segments 124, 123 and to a lead-in port 61 which is configured to be located laterally and outwardly of the access opening 111 so as to permit an endotracheal tube 300 (as shown in FIG. 8) introduced therein to be removable laterally between the first and second prepharyngeal segments 123, 143.

The juxtaposed wall 22 extends from the groove-side wall section 21 in the transverse direction, and extends in the lengthwise direction so as to be adjoined to the partition wall 13 when the channel-side and groove-side wall sections 140, 21 are attached to each other.

In this embodiment, the first shell 10 has the tongue-side wall 12, the partition wall 13, the channel-side wall section 140, and the viewing window 15, which are formed into a single-piece construction.

The second shell 20 has the groove-side wall section 21 and the juxtaposed wall 22, which are formed into a single-piece construction. The cover wall 30 extends in the lengthwise direction and is configured to interconnect the tongue-side wall 12 and the channel-side wall section 140 to laterally cover the laryngoscope guiding channel 70.

Further, when the second shell 20 is attached to the first shell 10, a conduit 50 is defined by the groove-side wall section 21, the partition wall 13, and the channel-side wall section 140 and is located between the laryngoscope guiding channel 70 and the endotracheal tube guiding groove 60 so as to permit an aspirator tube 200 (as shown in FIG. 8) that is led to pass through the conduit 50 to reach the patient's trachea for sucking out phlegm. The conduit 50 extends towards the second entry end 141 to terminate at an access port 40 which is located radially and outwardly of the access opening 111.

Further, the groove-side wall section 21 has an outer surface which extends in the lengthwise direction and which has an insertion groove 213 that extends towards the endotracheal tube guiding groove 60 to serve as a guideway. The insertion groove 213 extends toward the second entry end 141 to terminate at an entering port 214 which is disposed radially and outwardly of the access opening 111, and to extend to the second juncture region 145 to thereby permit an esophageal tube 100 (as shown in FIG. 8) which is inserted into the insertion groove 213 to be guided towards the opening of the patient's esophagus.

Preferably, a holder 16 in the form of a hook is disposed upstream of the endotracheal tube guiding groove 60 and is located at the first entry end 121 for holding the endotracheal tube 300.

Preferably, the first entry end 121 of the tongue-side wall 12 has a serrated outer surface 17, and the second entry end 141 has serrated outer surfaces 18,23 disposed respectively on the channel-side and groove-side wall sections 140,21 for facilitating gripping by an operator.

Figure 6:
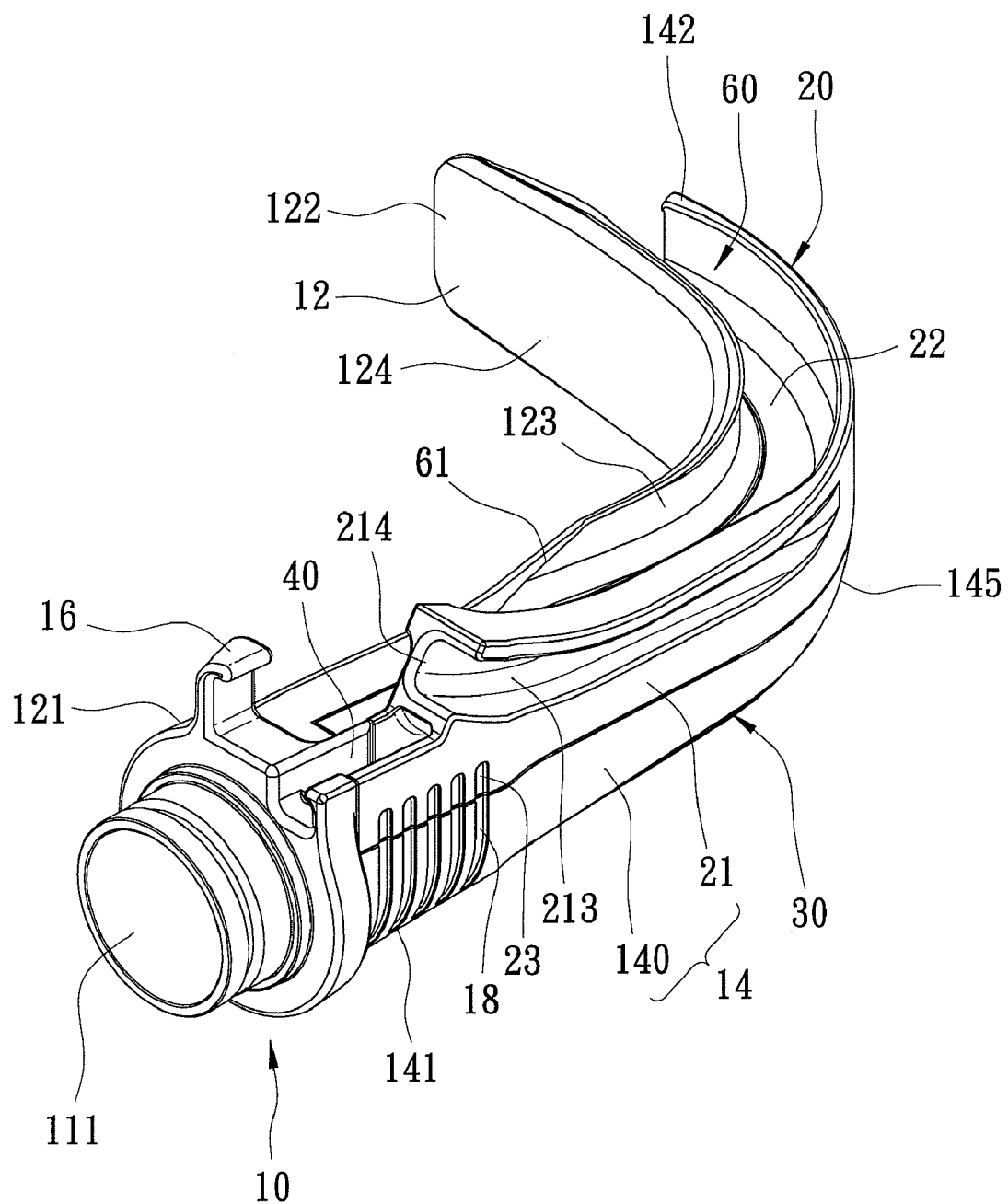
FIG. 6 is a perspective view of the preferred embodiment taken from another angle.

Referring to FIGS. 6 to 8, the pharyngeal intubation guiding device according to this invention may be used in a manner as described below:

1. An esophageal tube 100 may be inserted into the insertion groove 213 to be guided towards the opening of the patient's esophagus.

2. An aspirator tube 200 may be inserted via the access port 40 to be led along the conduit 50 to reach the patient's trachea to suck out phlegm.

3. An endotracheal tube 300 may be introduced through the endotracheal tube guiding groove 60 into the trachea of the patient. It is noted that the endotracheal tube 300 can be held by the holder 16 when the operator introduces other tubes into the patient to prevent movement of the endotracheal tube 300 relative to the guiding device so as not to cause discomfort to the patient.

4. A laryngoscope device 400 may be introduced via the access opening 111 to be led along the laryngoscope guiding channel 70 into the guiding device. It is noted that a distal end of the laryngoscope device 400 will be blocked by the viewing window 15 so that the interior of the patient can be observed through the viewing window 15.

As illustrated, the pharyngeal intubation guiding device according to this invention has the following advantages:

1. The guiding device of this invention permits insertion of the esophageal tube 100, the aspirator tube 200, the endotracheal tube 300 and the laryngoscope device 400 at the same time so that multiple intubation can be performed to facilitate medical treatment.

2. The endotracheal tube guiding groove 60 which has the lead-in port 61 configured to be located laterally and outwardly of the access opening 111 permits the endotracheal tube 300 to be removable laterally. In addition, since the tongue-side wall 12 and the groove-side wall section 21 which cooperatively define the endotracheal tube guiding groove 60 are configured to extend smoothly in the lengthwise direction, injury to the patient can be avoided during endotracheal intubation.

3. The insertion groove 213 is formed in an outer contour of the groove-side wall section 21 and has a lateral opening so that removal of the esophageal tube 100 from the guiding device is facilitated.

4. By virtue of the serrated outer surfaces 17,18,23, a large gripping surface is provided to facilitate gripping of the pharyngeal intubation guiding device by an operator.

5. The first shell 10, the second shell 20 and the cover wall 30 can be made in an injection molding process, and can be assembled in a convenient manner.

6. By virtue of the provision of the holder 16, the endotracheal tube 300 can be held in place when the operator introduces other tubes into the patient.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A pharyngeal intubation guiding device comprising:
tongue-side and palate-side walls which extend in a lengthwise direction, and which are spaced apart from each other in a transverse direction that is a direction transverse to the lengthwise direction to define a guiding duct, said tongue-side wall having first entry and locating ends opposite to each other in the lengthwise direction, and first prepharyngeal and postpharyngeal segments extending respectively from said first entry end and first locating ends and towards each other to form a first juncture region which is configured to conform to the rear end of a patient's tongue such that said first locating end is brought to engage the front of the patient's epiglottis to thereby permit said guiding duct at said postpharyngeal segment to confront the opening of the patient's larynx, said palate-side wall having second entry and locating ends which are opposite to each other in the lengthwise direction, said second entry end cooperating with said first entry end to define an access opening which is in spatial communication with said guiding duct, said second locating end being configured to disposed at the opening of the patient's larynx to serve as a barrier between the larynx and the esophagus of the patient when said first locating end is engaged with the front of the patient's epiglottis, and second prepharyngeal and postpharyngeal segments extending respectively from said second entry end and said second locating end and towards each other to form a second juncture region which is configured such that an outer contour of said second prepharyngeal segment establishes a guideway towards the opening of the patient's esophagus;
a laryngoscope guiding channel which is disposed in said guiding duct, and which extends from said first postpharyngeal segment to said first prepharyngeal segment and through said access opening;
a viewing window which extends between said first and second postpharyngeal segments in the transverse direction so as to define a terminal end of said laryngoscope guiding channel that is located upstream of said first locating end;
an endotracheal tube guiding groove which is disposed in said guiding duct, and which extends from said first locating end along said first postpharyngeal and prepharyngeal segments and to a lead-in port which is configured to be located laterally and outwardly of said access opening so as to permit an endotracheal tube introduced therein to be removable laterally between said first and second prepharyngeal segments; and
a partition wall which extends between said tongue-side wall and said palate-side wall and in the lengthwise direction to divide said guiding duct into said laryngoscope guiding channel and said endotracheal tube guiding groove;
said palate-side wall including channel-side and groove-side wall sections which are attachable to each other along a joining line extending in the lengthwise direction, said channel-side wall sections confronting said tongue-side wall in the transverse direction to define said laryngoscope guiding channel, said groove-side wall section confronting said tongue-side wall in the transverse direction to define said endotracheal tube guiding groove.

2. The pharyngeal intubation guiding device according to claim 1, further comprising a cover wall which extends in the lengthwise direction and which is configured to interconnect said tongue-side and palate-side walls to laterally cover said laryngoscope guiding channel.

3. The pharyngeal intubation guiding device according to claim 2, wherein said tongue-side wall, said partition wall, said channel-side wall section, and said viewing window are formed into a single-piece construction.

4. The pharyngeal intubation guiding device according to claim 3, further comprising a juxtaposed wall which extends from said groove-side wall section in the transverse direction, and which extends in the lengthwise direction so as to be adjoined to said partition wall when said channel-side and groove-side wall sections are attached to each other, and wherein said juxtaposed wall and said groove-side wall section are formed into a single-piece construction.

5. The pharyngeal intubation guiding device according to claim 4, wherein said groove-side wall section has an outer surface which extends in the lengthwise direction and which has an insertion groove that extends towards said endotracheal tube guiding groove to serve as said guideway, said insertion groove being configured to extend toward said second entry end to terminate at an entering port which is disposed radially and outwardly of said access opening, and to extend to said second juncture region to thereby permit an esophageal tube which is inserted into said insertion groove to be guided towards the opening of the patient's esophagus.

6. The pharyngeal intubation guiding device according to claim 5, further comprising a conduit which is disposed in said guiding duct and between said laryngoscope guiding channel and said endotracheal tube guiding groove and which extends in the lengthwise direction so as to permit an aspirator tube that is led to pass through said conduit to reach the patient's trachea for sucking out phlegm.

7. The pharyngeal intubation guiding device according to claim 6, wherein said conduit extends towards said second entry end to terminate at an access port which is located radially and outwardly of said access opening.

8. The pharyngeal intubation guiding device according to claim 4, further comprising a holder which is disposed upstream of said endotracheal tube guiding groove and which is located at said first entry end for holding the endotracheal tube.

9. The pharyngeal intubation guiding device according to claim 4, wherein said first and second entry ends respectively have serrated outer surfaces for facilitating gripping by an operator.

* * * * *